US00PP18179P3

(12) United States Plant Patent
Jensen

(10) Patent No.: US PP18,179 P3
(45) Date of Patent: Nov. 6, 2007

(54) MINIATURE ROSE PLANT 'JENEIGHT'

(50) Latin Name: *Rosa hybrida*
Varietal Denomination: JENeight

(76) Inventor: Svend Jensen, Kongensgade 32, Christiansfeld (DK), 6070

( * ) Notice: Subject to any disclaimer, the term of this patent is extended or adjusted under 35 U.S.C. 154(b) by 109 days.

(21) Appl. No.: 11/173,508

(22) Filed: Jul. 1, 2005

(65) Prior Publication Data

US 2007/0006352 P1 Jan. 4, 2007

(51) Int. Cl.
*A01H 5/00* (2006.01)

(52) U.S. Cl. ..... Plt./117

(58) Field of Classification Search ..... Plt./117, Plt./124, 103

See application file for complete search history.

*Primary Examiner*—Howard J. Locker
(74) *Attorney, Agent, or Firm*—Venable LLP

(57) ABSTRACT

A new miniature rose plant which has abundant, long lasting, white colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Figures 1, 2, 3, 4, 5, 6, 7, 8, 9:
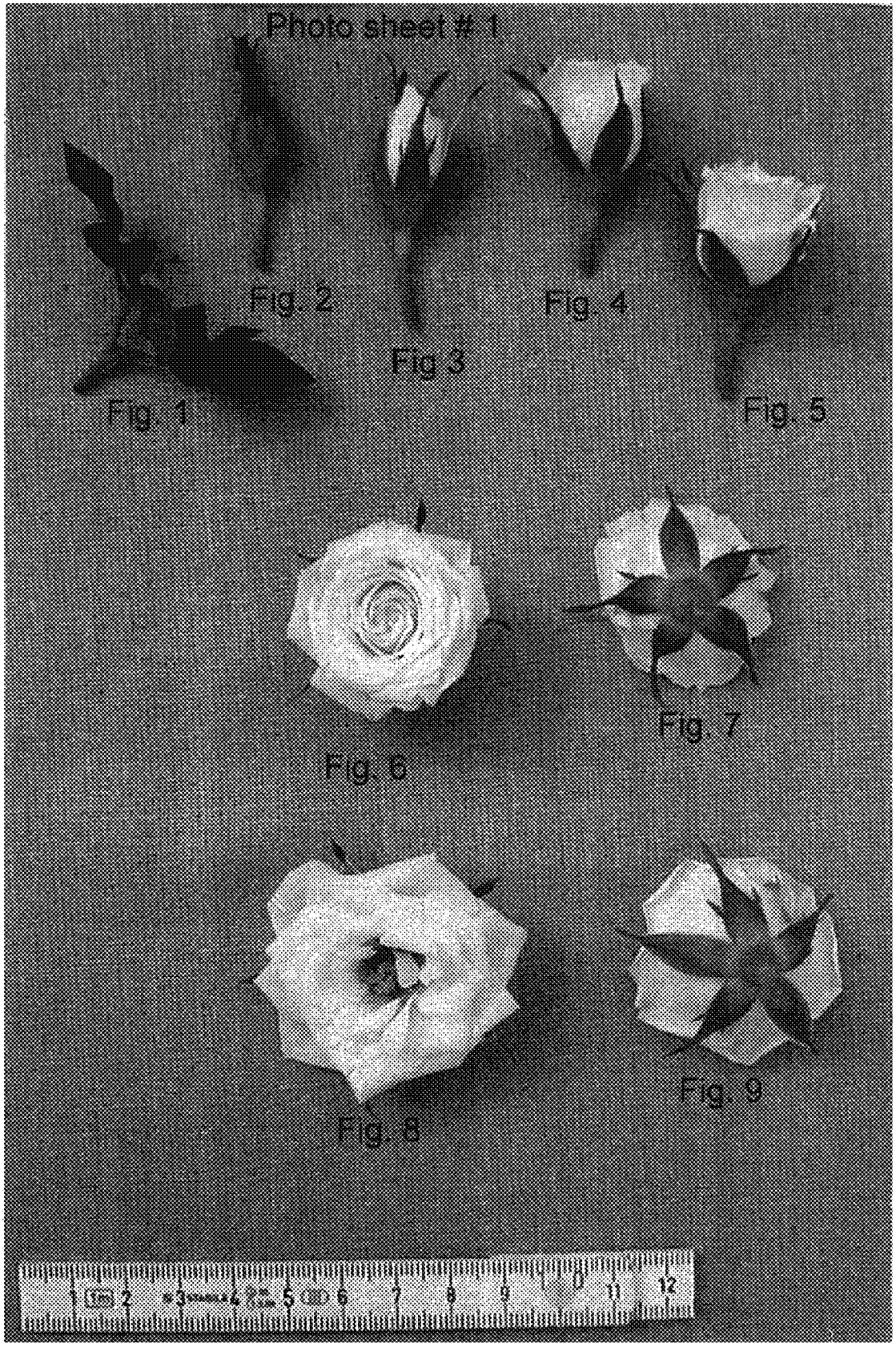

Latin name of genus and species: *Rosa hybrida* 'JENeight.'

Variety denomination: The new variety is named JENeight.

BACKGROUND OF THE INVENTION

The present invention constitutes a new and distinct variety of miniature rose plant, which was developed by artificially pollinating an unnamed seedling (not patented in the US) with an unnamed seedling (not patented in the US). The two parents were crossed during the summer of 2001, and the resulting seed was sown in December 2001, in a controlled glasshouse environment. Out of the resulting seedlings one seedling was selected, as a distinct new variety and was named JENeight.

The variety can be distinguished from its seed parent, an unnamed seedling, by the following combination of characteristics:

JENeight has small double flowers, while the unnamed seed parent has medium sized single flowers; and JENeight has white colored petals, while the unnamed seed parent has pink petals.

The new variety may distinguished from its pollen parent, an unnamed seedling created by the same inventor, by the following combination of characteristics:

JENeight has smaller flowers and foliage as compared to the unnamed pollen parent; and JENeight has white colored petals, while the unnamed pollen parent has pale pink petals.

BRIEF SUMMARY OF THE INVENTION

Initial asexual reproduction of JENeight by cuttings was first carried out by the inventor in Christiansfeld, Denmark. The reproduction was conducted under controlled greenhouse conditions. Having demonstrated asexual reproduction it was found that all characteristics and distinctions came true to form and were established in succeeding propagations. JENeight is a low and compact miniature rose with medium vigor. Tests show that the shelf life of the entire plant is average as compared to similar varieties and that the lastingness of a single flush of flowers is also average as compared to similar varieties.

The objective of the hybridization of this rose variety for commercial greenhouse culture was to create a new and distinct variety with:

Uniform and abundant flowers with good keeping properties;

Attractive long lasting foliage and overall compact growth;

Year round flowering under glasshouse conditions;

Suitability for production from softwood cuttings in pots; and

Durable flowers and foliage which make the variety suitable for distribution in the floral industry.

This combination of qualities was not present in previously available commercial cultivars of this type and distinguishes JENeight from all other varieties of which the inventor is aware. The seeds from hybridization were planted in a controlled environment and evaluations were conducted on the resulting plants. JENeight was selected by Svend Jensen, in his development program in Christiansfeld, Denmark.

BRIEF DESCRIPTIONS OF THE DRAWINGS

The accompanying color illustrations show as true as is reasonably to obtain in color photographs of this type, the typical characteristics of the buds, flowers, leaves, stems of JENeight. Specifically illustrated in:

Photo sheet #1:

FIG. 1: Young shoot.

FIG. 2: Bud before opening of the sepals.

FIG. 3: Bud at the stage of opening of the sepals.

FIG. 4: Bud at the stage of opening the petals.

FIG. 5: Flower during course of opening.

FIG. 6: Opening flower—plan view—obverse.

FIG. 7: Opening flower—plan view—reverse.

FIG. 8: Fully open flower —plan view—obverse.

FIG. 9: Fully open flower —plan view—reverse.

Figures 10, 11, 12, 13, 14, 15, 16, 17, 18:
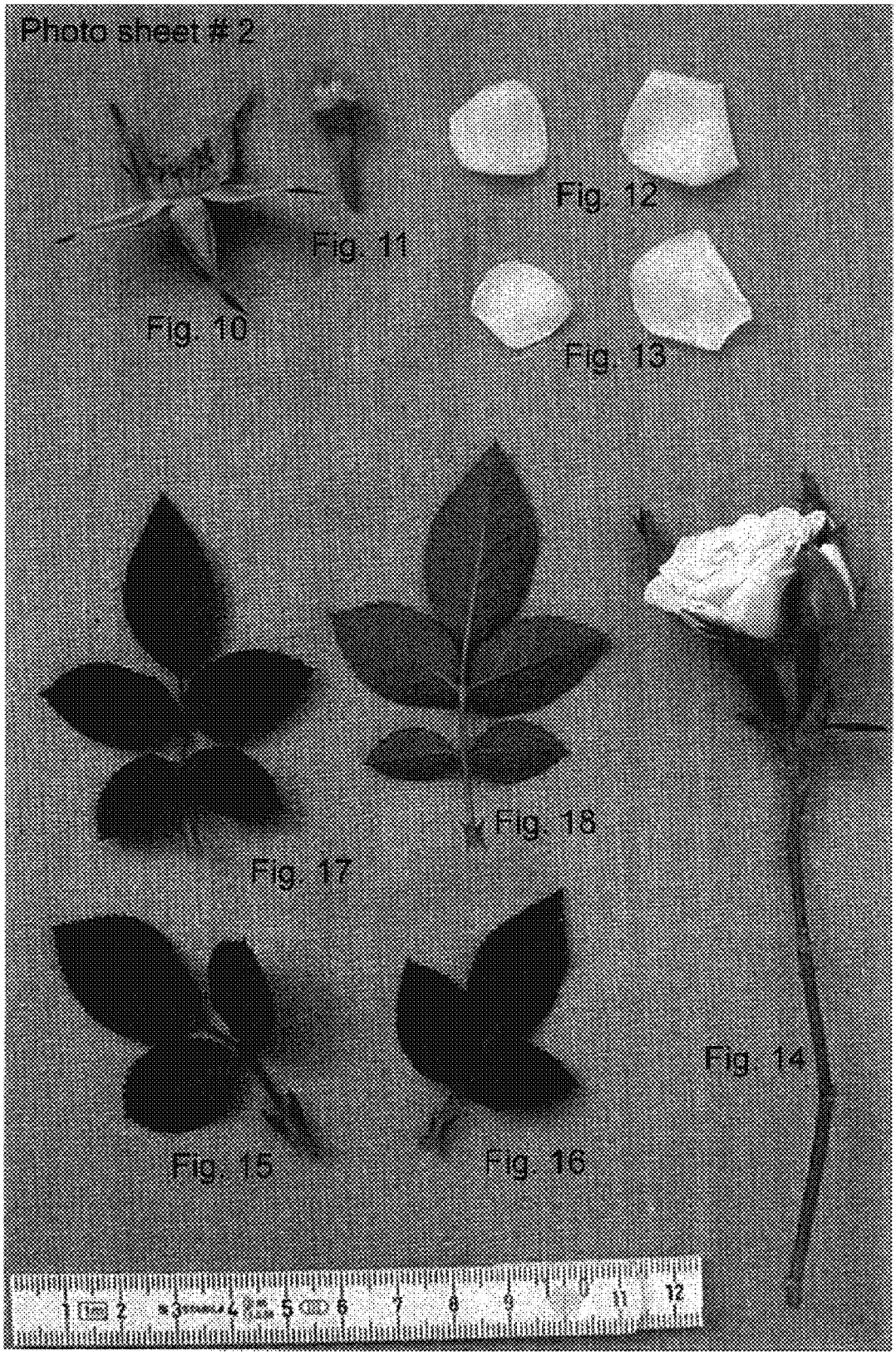

Photo sheet #2:

FIG. 10: Receptacle showing stamens and pistils.

FIG. 11: Receptacle showing pistils (stamens and sepals removed).

FIG. 12: Flower petals, detached—inner surface.

FIG. 13: Flower petals, detached—outer surface.

FIG. 14: Bare stem exhibiting thorns and flower attachment.

FIG. 15: Leaf with three leaflets upper surface.

FIG. 16: Leaf with three leaflets reverse surface.

FIG. 17: Leaf with five leaflets upper surface.

FIG. 18: Leaf with five leaflets reverse surface.

DETAILED BOTANICAL DESCRIPTION OF THE VARIETY

The following is a detailed description of the Miniature Rose: *Rosa hybrida* 'JENeight'. The following observations, measurements, values and comparisons describe plants grown in glass houses in Christiansfeld, Denmark. Plants were observed 11 to 13 weeks after propagation by cuttings and growth in containers 10 centimeters in diameter.

Color references are made using The Royal Horticultural Society (London, England) Colour Chart, 1995, except where common terms of color are used.

For a comparison, the nearest existing rose variety is 'Poulgo001', a rose variety described and illustrated in U.S. Plant Pat. No. 13,453.

Chart I details several physical characteristics of JENeight versus Poulgo001.

CHART 1

| | JENeight | Poulgo001 |
|---|---|---|
| Petal color, Upper surface | White Group 155D | White Group 155C |
| Petal color, Reverse surface | White Group 155D | White Group 155C |
| Petal count | 25-30 | 60-65 |

Seed parent: Unnamed seedling.
Pollen parent: Unnamed seedling.
Classification:
*Botanical.*—*Rosa hybrida.*
*Commercial.*—Miniature.

PLANT

Plant growth: Moderately vigorous. Grows compact upright to bushy. When grown as 10 cm pot plant, the average height of the plant itself is 18 to 20 cm, and average width is 20 cm. When grown in a 15 cm diameter pot, the average height of the plant itself is 22 to 27 cm and the average width is 30 cm.

Production time: Generally 11 to 13 weeks depending on average temperature, light level and cultural practices.

Stem:

*Color.*—Young wood: Yellow-Green Group 148A. Older wood: Yellow-Green Group 148B.

*Thorns.*—Incidence: high number of thorns per stem. Size: 2–3 mm. Color: White Group 155A. Shape: Deep concave.

*Surface.*—Young wood: Smooth. Older wood: Smooth.

*Dimensions.*—Diameter: 2–3 mm. Internode length: 20–30 mm. Numbers of internodes: 5–6.

Plant foliage: Leaves arranged alternately, compound with 3 to 5 leaflets per leaf, generally symmetrical, abundant, and flat in aspect with stipules at petiole base.

*Quantity of leaves.*—5–6 per lateral branch.

*Leaf size.*—Medium (60–65 mm (length) by 40–50 mm (width) for five leaflets.

*Petioles.*—Color: Yellow Green Group 148A. Margins: entire. Length: 10–12 mm. Diameter: about 1–2 mm.

*Stipules.*—Size: 4–5 mm. Surface: Smooth. Color: Yellow Green Group 148C. Margins: Entire.

*Rachis.*—Color: Yellow Green Group 148A. Margins: Entire. Length: 8–10 mm. Diameter: 0.5–1 mm.

*Leaflets.*—Edge: Serrated. Serration: Single. Shape: Ovate with acute apex and obtuse base. Texture: Smooth. Appearance: Dull. Size: 30–65 mm. (length) by 30–55 mm (width). Color: Young foliage: Upper surface: Yellow-Green Group 148B. Lower surface: Greyed-Green Group 198A. Color: Mature foliage: Upper surface: Yellow-Green Group 148A. Lower surface: Greyed Green Group 198A.

INFLORESCENCE

Blooming habit: Recurrent.

Number of flowers: Generally 3–5 buds per flowering stem.

*Peduncle.*—Color: Yellow Green Group 148B. Texture: Smooth. Length: 10–15 mm. Orientation: Upright.

*Receptacle.*—Surface: Smooth, glabrous. Shape: Cup-shaped. Size: 6–7 mm (height) by 7–9 mm (width). Color: Yellow Green Group 148B.

*Sepals.*—Number: 5. Shape: Narrowly Ovate with acute tip. Texture: Leathery. Margin: Foliaceous appendages on two of the five sepals. Appearance: Dull. Color: Upper surface: Yellow Green Group 148A. Reverse surface: Greyed Green Group 191D. Size: 12.5 mm (length), by 7 mm (width).

*Buds.*—Size (during opening): 18–20 mm (height) by 10–12 mm (width). Shape: Ovoid and blunt. Color: at ¼ open, White Group 155D.

*Flower.*—Duration of entire flush: 11–15 days. Fragrance: None. Size: 50–55 mm in diameter. Form: (Shape of flower viewed from the side). During opening: Cup-shaped. Fully opened: Saucer-shaped. Color of petals during opening: Upper surface: White Group 155D. Reverse surface: White Group 155D. Color of petals after opening: Upper surface: White Group 155D. Reverse surface: White Group 155D. Basal Petals spots: Size: 1–2 mm. Color: Yellow-White Group 158B. General tonality of open flower: Third day: White Group 155D. Afterwards: White Group 155D. Petal reflex: Outermost petals reflexed backwards during opening. All petals reflexed backwards when flower is fully open. Petal texture: Smooth. Petal edge: Entire. Petal count: 25–30 on the average flower. Petal size: 20–25 mm (length) by 20–25 mm (width). Petal shape: Outer petals: round. Inner petals: ovate. Apex: orbicular. Base: obtuse to rotundate. Reproductive organs: Stamen number: approximately 50 on average per flower. Pollen color: Yellow Orange Group 20D.

Pollen abundance: average. Anther size: 1–2 mm. Anther color: Greyed Orange Group 170C. Anther shape: oblong. Filament size: 4–5 mm. Filament color: Green-White Group 157B. Pistils number: Approximately 30 on average per flower. Stigma location: Inferior relative to anthers. Stigma color: Green-White Group 157D. Style color: Greyed-Purple Group 186D. Style length: 2 to 3 mm.

DEVELOPMENT

Vegetation: Dense.

Blooming: Abundant.

Hips/seeds: Fruit set has not been observed because the plant has never been grown to the stage of seed development since the variety was developed for use as a flowering pot plant only.

Disease resistance: Above average resistance to mildew and Botrytis under normal growing conditions in Christiansfeld, Denmark.

Winter hardiness and drought/heat tolerance: Not evaluated because the variety is a potted flowering plant developed for a one time use only.

What is claimed is:

1. A new and distinct variety of rose plant of the miniature class, substantially as herein illustrated and described as a distinct and novel rose variety due to its abundant, long lasting, white color flowers, attractive long lasting matte foliage, vigorous and compact growth, year round flowering under glasshouse conditions, suitability for production from softwood cuttings in pots, and durable flowers and foliage which make the variety suitable for distribution in the floral industry.

* * * * *

Photo sheet # 1

Photo sheet # 2